United States Patent
Barger et al.

(10) Patent No.: US 8,206,659 B2
(45) Date of Patent: Jun. 26, 2012

(54) DEVICES FOR CRYSTALLIZATION BY CONTROLLED EVAPORATION

(75) Inventors: Jack Barger, Poway, CA (US); James Sinclair, Carlsbad, CA (US); Michael P. Emery, Santee, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 540 days.

(21) Appl. No.: 12/483,787

(22) Filed: Jun. 12, 2009

(65) Prior Publication Data
US 2010/0314051 A1   Dec. 16, 2010

(51) Int. Cl.
*B01D 9/00* (2006.01)
(52) U.S. Cl. .................................. 422/245.1; 422/648
(58) Field of Classification Search ............. 422/244.09, 422/245.1, 648
See application file for complete search history.

(56) References Cited

OTHER PUBLICATIONS

Kem-Vap Solvent Evaporator; J-Kem Scientific, Inc. website; http://www.jkem.com/kemvap.html, received Jan. 26, 2009.

*Primary Examiner* — Edward Johnson
(74) *Attorney, Agent, or Firm* — Knobbe Martens Olson & Bear LLP (57) ABSTRACT

Methods and devices for controlled evaporation of solvent from a solution are provided. In one embodiment, the device can control evaporation of different solutions comprising solvents of dissimilar volatilities simultaneously. In another embodiment, control over the flow of solvent vapor out of the device is provided by selecting the pressure at an inlet port and an exhaust port of the device. In yet another embodiment, control over the flow of solvent vapor out of the device is provided by selecting the size of a disk flow control orifice positioned between the wells and a vapor removal outlet of the device. In still another embodiment, control over the flow of solvent vapor out of the device is provided by the opening and closing of the vapor removal outlet of the device. In yet a further embodiment, the rate of evaporation of solvent is controlled by controlling the temperature of the solution. The flow rate control mechanisms can be used alone or in any combination to control evaporation of one or more solvents from solutions.

30 Claims, 4 Drawing Sheets

DEVICES FOR CRYSTALLIZATION BY CONTROLLED EVAPORATION

BACKGROUND OF THE INVENTION

1. Field of the Invention

The present invention relates generally to the crystallization of drug substances and, more particularly, relates to methods and devices for crystallization by controlled evaporation.

2. Description of the Related Art

High quality crystals are used in a variety of studies throughout the process of developing a drug. In early development, solid forms of lead compounds are available in fairly small quantities. These solid forms are studied to determine which forms are most suitable to move forward in development. In late development, a well-characterized form is selected for large scale manufacturing.

Crystals are typically grown by dissolving the drug substance in a suitable solvent, then evaporating the solvent. In a conventional, manual process for forming crystals, a scintillation vial is partially filled with the drug and solvent solution and capped with aluminum foil. A small hole is poked in the foil. The vial then sits for some length of time. The slow evaporation of the solvent through the small hole in the foil favors crystal growth. There are many disadvantages, however, to the conventional method. The lack of controls for making the hole, and therefore the lack of consistency in hole size, leads to widely varying rates of evaporation, even for the same drug substance and solvent. Experimental reproducibility is thus a serious challenge. Further, the method cannot be scaled for use in small sample volumes, because the holes in the aluminum foil are no longer "small," relatively speaking, when the sample volume is reduced to that of a well in a 96-well plate. In fact, in sample volumes below 0.5 mL, evaporation using holes poked in aluminum foil is generally too fast to permit formation of high quality crystals. The problem of rapid evaporation is particularly severe when the solvent is very volatile.

Current instruments that automate the process of crystal formation also suffer significant drawbacks. One device, for example, feeds inert gas close to the surface of the wells in a 96-well plate using a manifold with a common exhaust. This allows for controlled evaporation, however, only if the wells are filled with one solvent or multiple solvents of similar volatilities. Thus, among other disadvantages, current designs cannot accomplish controlled evaporation of multiple solvents of dissimilar volatilities simultaneously. Thus, slow, controlled evaporation of multiple solvents of varying volatilities from small volume wells of, for example, a 96-well plate, remains a significant challenge in the creation of high quality crystals.

SUMMARY OF THE INVENTION

In accordance with one aspect of the present invention, methods and devices are provided for controlled evaporation of a solvent from a solution.

One embodiment is a device for controlled evaporation of solvent from at least one solution. The device includes a plurality of wells configured to hold the at least one solution; an inlet port for a first set of one or more of the plurality of wells; an exhaust port for a second set of one or more of the plurality of wells; and at least one flow control orifice positioned between the inlet port and the exhaust port.

In another embodiment, a method for controlled evaporation of solvent from at least one solution is provided. The method includes filling a selected first set of wells in a multi-well plate with a first solution including at least one solvent. The method also includes attaching an inlet manifold to the plate, where the inlet manifold includes an inlet port connected to and in fluid communication only with each of the wells in the selected first set of wells. The method further includes attaching an exhaust manifold to the plate, where the exhaust manifold includes an exhaust port connected to and in fluid communication only with each of the wells in the selected first set of wells; introducing a gas into the inlet port; and removing solvent vapor from the selected first set of wells.

Yet another embodiment is a device for controlled evaporation of solvent from at least one solution. The device includes a plate comprising a plurality of wells, where a selected first set of wells hold a first solution including at least one first solvent. The device also includes a first gas inlet connected to and in fluid communication only with the selected first set of wells; a first vapor removal outlet connected to and in fluid communication only with the selected first set of wells; and a means for controlling the rate at which solvent vapor flows from the first set of wells to the vapor removal outlet.

In still another embodiment a device for controlled evaporation of solvent from at least one solution is provided. The device includes a plate comprising a first set of wells and a second set of wells, where the first set of wells hold a solution comprising at least one first solvent and the second set of wells hold a different solution comprising at least one second solvent different from the at least one first solvent. The device also includes a set of gas inlets connected to and in fluid communication only with a corresponding set of wells; a set of vapor removal outlets separately connected to and in fluid communication with the same corresponding set of wells; and means for separately controlling vapor removal from the first and second sets of wells.

DETAILED DESCRIPTION OF THE PREFERRED EMBODIMENT

Any feature or combination of features described herein are included within the scope of the present invention provided that the features included in any such combination are not mutually inconsistent as will be apparent from the context, this description, and the knowledge of one skilled in the art. In addition, any feature or combination of features may be specifically excluded from any embodiment of the present invention. For purposes of summarizing the present invention, certain aspects, advantages and novel features of the present invention are described herein. Of course, it is to be understood that not necessarily all such aspects, advantages, or features will be embodied in any particular embodiment of the present invention.

In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

Figure 1:
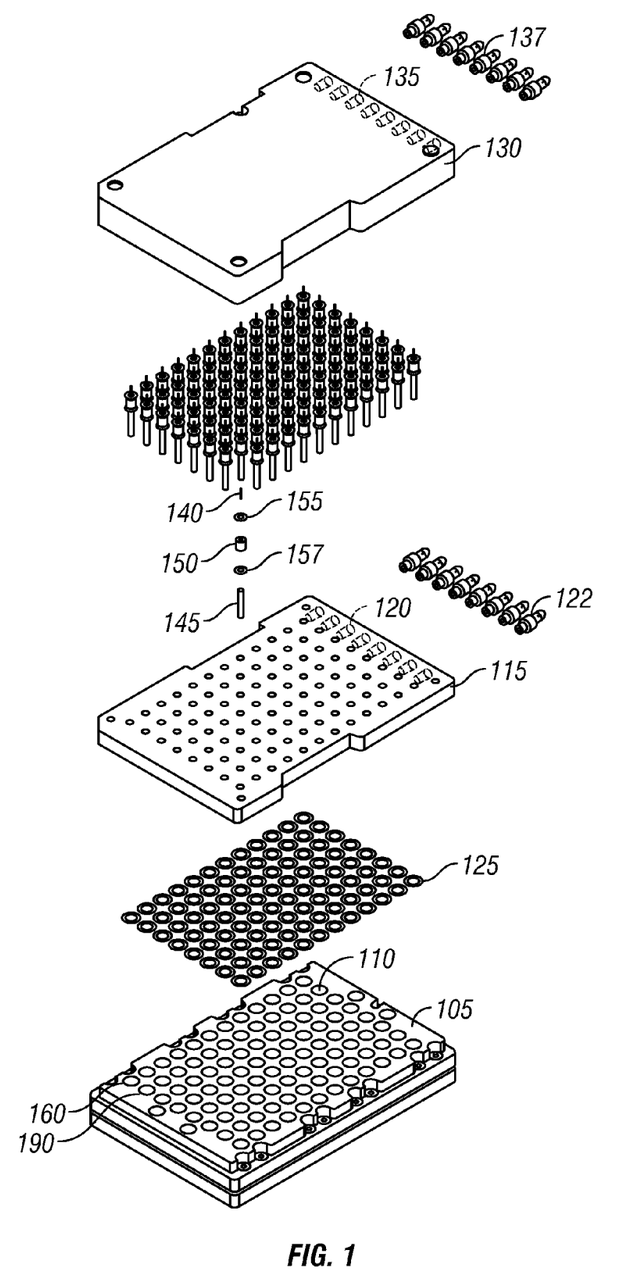
FIG. 1 is an exploded perspective view of an embodiment of a controlled evaporation device.

FIG. 1 is an exploded view of one embodiment of a device 100 for controlled evaporation of a solvent from a solution in accordance with the invention. The device 100 includes a plate 105. In one embodiment, the plate 105 comprises ninety-six wells 110 arranged in rows and columns. The wells 110 are configured to hold solutions such as, for example, a drug substance dissolved in solvent. The solvent may be consist essentially of one substance such as water, DMSO, alcohol, or the like, or may be a mixture of different substances. In some aspects of the present invention, the solvent in the solution evaporates, leaving crystals of the drug substance in the wells 110. The solutions contained in the plate 105 can be dissimilar, and can include drug substances dissolved in different solvents of varying volatilities.

Figure 2:
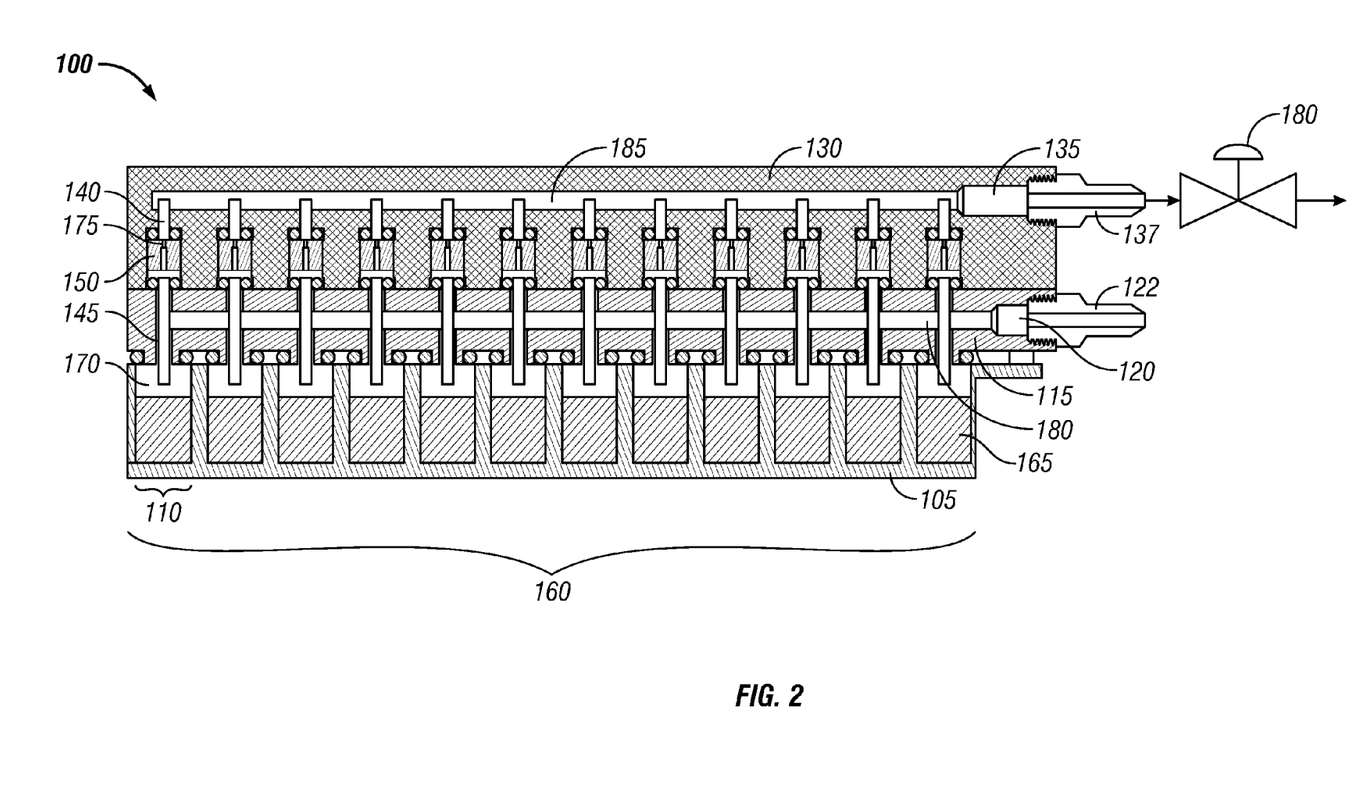
FIG. 2 is a cross-sectional view of one row of the device of FIG. 1.
Figure 3:
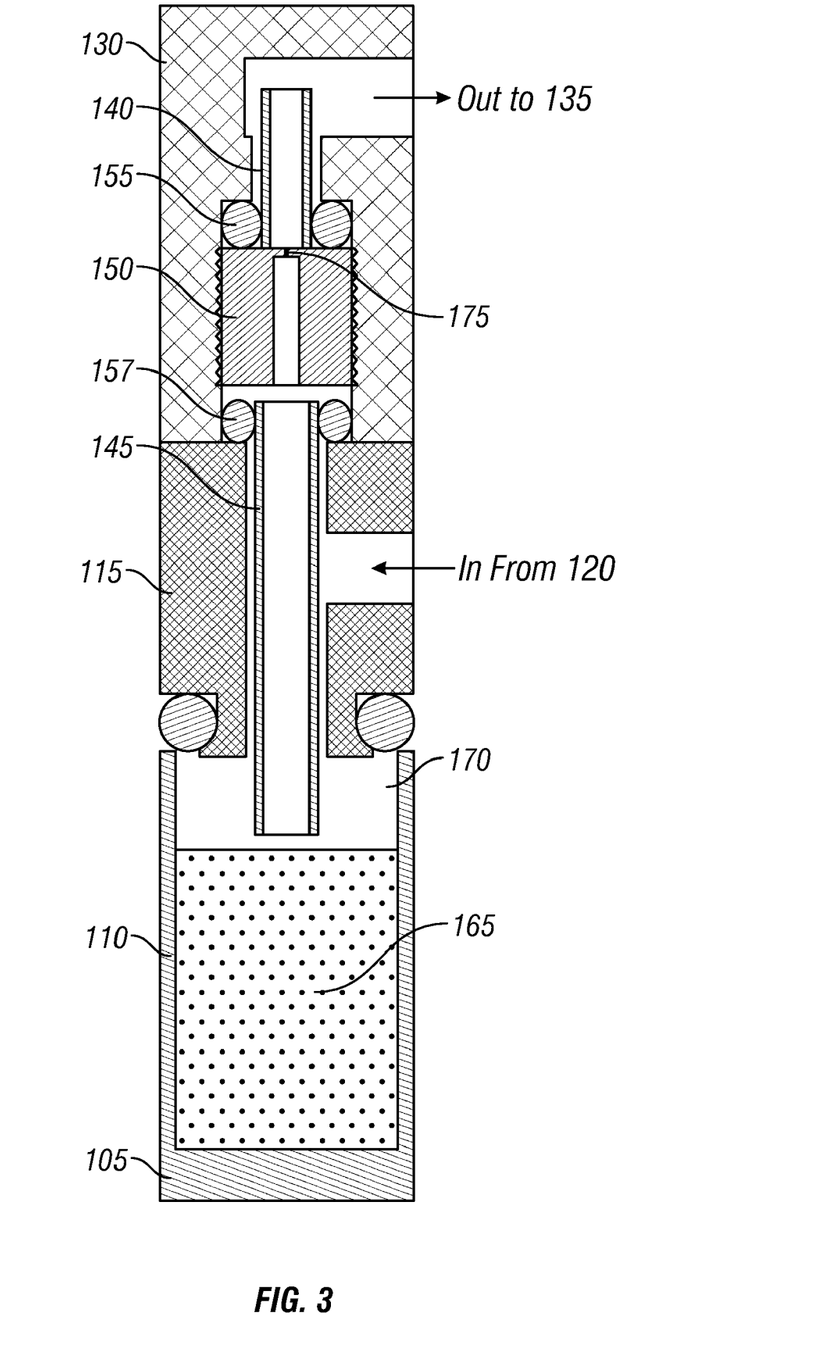
FIG. 3 is a cross-sectional view of the leftmost well of the row illustrated in FIG. 2.

The device 100 also includes an inlet manifold 115 that can be positioned over and connected to the plate 105. The inlet manifold 115 includes one or more inlet ports 120. The inlet ports are connected to channels within the inlet manifold configured to allow for the introduction of ambient air or a gas into the wells 110. The channels are not shown in FIG. 1 but are shown in FIGS. 2 and 3. Seals 125, which may comprise o-rings, may be provided to create a seal between the inlet manifold 115 and the plate 105. The seals 125 may prevent gas and/or solvent vapor from escaping between the inlet manifold 115 and the plate 105.

The device 100 according to one embodiment includes an exhaust manifold 130. The exhaust manifold 130 can include one or more exhaust ports 135, or vapor removal outlets, configured to allow for the removal of gas and/or solvent vapor from the wells 110. The exhaust ports 135 are connected to channels within the exhaust manifold which are not shown in FIG. 1 but are shown in FIGS. 2 and 3. The exhaust manifold 130 is positioned over and connected to the inlet manifold 115. Seals 155, 157, which may comprise o-rings, spring energized seals, or the like, may be provided to prevent gas and solvent vapor from escaping between the exhaust manifold 130 and the inlet manifold 115. The seals 155, 157 may also ensure gas and solvent vapor only leave the exhaust manifold 130 through the exhaust port(s) 135. In addition, the inlet ports 120 and the exhaust ports 135 may be coupled to fittings 122, 137, respectively.

The device 100 can also include an upper outlet tube 140, a flow control disk 150, and a lower outlet tube 145 configured to allow for the removal of gas and solvent vapor from the wells 110. Thus, in some aspects, the exhaust port 135 is opened to allow gas to flow from the inlet port 120; through the lower outlet tube 145, the disk 150, and the upper outlet 140; and finally to the exhaust port 135 and out of the device 100. As the gas flows out of the device, it can carry air with solvent vapor to the exhaust port 135 and out of the device 100. As explained further below, the exhaust port 135 can be opened at specific times and for specific durations depending on the volatility of a solvent in the well 110. In one embodiment, the frequency and duration of the open periods is programmed so that solvent vapor leaves the device at a precisely controlled rate.

The disk 150 includes an orifice for flow control that allows gas and solvent vapor to flow to the exhaust port 135 and out the device 100. According to one embodiment, the disk 150 is a sapphire disk. The orifice in disk 150 may be precision-drilled with a diameter selected to produce a desired rate at which gas and solvent vapor flow out of the well when the exhaust port 135 is opened.

The elements of the embodiment of FIG. 1 will now be described in more detail with reference to FIGS. 2 and 3. FIG. 2 is a cross-sectional view of one row 160 of the device 100 illustrated in FIG. 1. In the embodiment illustrated in FIG. 2, twelve wells 110 are arranged in one of eight rows 160 of the plate 105. Each of the twelve wells 110 can hold a solution 165 or, alternatively, a subset of the twelve wells 110 can hold a solution 165. FIG. 3 is a cross-sectional view of the leftmost well of the row 160 illustrated in FIG. 2. According to one embodiment, the well 110 is one of ninety-six wells in the plate 105. The plate 105 can be made of any suitable material, including plastic or a metal, such as aluminum. The plate 105 and/or the wells 110 may include various types of coatings such as PTFE, other plastic materials, or metals such as gold so that they are inert to the solution(s) 165.

Referring now to FIGS. 2 and 3, the well 110 includes a head space 170 between the solution 165 and the inlet manifold 115. In embodiments where the solution 165 comprises a drug substance dissolved in a solvent, a portion of the solvent in the solution 165 evaporates into the space 170 above the solution 165. During evaporation, solvent molecules leave the surface of the solution 165 and are present in the space 170 in gaseous or vapor form. More volatile solvents are characterized by higher evaporation rates and higher evaporated solvent concentrations in the head space 170.

As described above, the inlet manifold 115 includes an inlet port 120. A gas can be introduced into each well 110 in the row 160 through the inlet port 120. The intake manifold 115 according to some aspects includes a plurality of inlet channels 180, with each inlet channel 180 connected to and in fluid communication with one row and the wells associated with that row. Thus, gas can be introduced into the inlet port 120 and flow through the inlet channels 180 to the wells 110. The lower outlet tube 145 extends through the inlet manifold 115 into head space 170 above the solution 165. The disk 150 according to one embodiment is positioned above and in fluid communication with the lower outlet tube 145. The disk 150 includes an orifice 175. The orifice 175 may be a precision-drilled orifice to provide gas flow rate control from the head space 170 to the exhaust manifold 130. The exhaust manifold 130 comprises a plurality of exhaust channels 185, with each exhaust channel 185 connected to and in fluid communication with one row and the wells associated with that row. The disk 150 and the lower outlet tube 145 are in fluid communication with the upper outlet tube 140 and the exhaust channels 185 such that gas and solvent vapor can move from the space 170 to the exhaust manifold 130 and exit the device 100 through the exhaust port 135. The exhaust port 135 can be open to ambient pressure or subjected to a vacuum to draw the gas and solvent vapor out of the device 100.

The device 100 can also include an exhaust valve 180 configured to open and close the exhaust port 135. In some embodiments, the exhaust port 135 is open to ambient pressure when the exhaust valve 180 is open, allowing gas and solvent vapor to flow from the space 170 above the solution 165, through the lower outlet tube 145, the disk 150, the upper outlet tube 140, and the exhaust port 135 to the atmosphere. When the exhaust valve 180 is closed, gas and solvent vapor do not exit to the atmosphere.

Persons of skill in the art will understand that the device 100 is not limited to a specific number of rows or columns of wells, and that one inlet port 120 and/or one exhaust port 135 may be connected to and in fluid communication with more than one row or with portions of a row. Similarly, it will be understood that the plate 105 is not limited to an arrangement of "rows" and "columns," but can be arranged in any suitable manner. Wells in the plate 105 may be arranged in quadrants, for example, with one inlet port 120 and/or one exhaust port 135 connected to and in fluid communication with one quadrant.

The device 100 can be assembled in various ways. In one embodiment, the exhaust manifold 130 is assembled first, is then coupled to the inlet manifold, and the combination is attached to the plate. To assemble the exhaust manifold 130, the upper outlet tubes 140 are placed in the exhaust manifold 130, followed by the seals 155. The disks 150 may be threaded and screwed or press fit into countersunk holes provided in the exhaust manifold 130. The lower outlet tubes 145 are next placed in the exhaust manifold, held in place by additional seal 157. The exhaust manifold 130 is then placed over the inlet manifold 115 such that the lower outlet tubes 145 extend through openings in the inlet manifold 115 and into the head spaces 170 of the wells 110. The exhaust manifold 130 can then be secured to the inlet manifold 115 with fasteners such as screws or clamps. Next, the wells 110 of the plate 105 are filled with the solution(s) 165. Finally, the assembled manifolds 115, 130 are positioned over and connected to the plate 105 with fasteners such as screws or clamps. The inlet manifold 115 can include integrated seals 125 such that the seals 125 mate with the openings in the wells 110 when the inlet manifold 115 is connected to the plate 105. In another embodiment, the seals 125 are positioned over the openings in the wells 110 before the inlet manifold 115 is connected to the plate 105. Persons of skill in the art will understand that the device 100 need not be fully disassembled after each use. Thus, the assembled and coupled manifolds 115, 130 can remain assembled and be fastened to different plates 105 for each different evaporation sequence.

Solvent vapor can move from the space 170, through the lower outlet tube 145, the orifice 175 in the disk 150, and the upper outlet tube 140 to the exhaust port 135. If the exhaust port 135 is open to the ambient air, or if the exhaust valve 180, if provided, is open, the solvent vapor leaves the exhaust port 135 and the device 100. If the exhaust port is left open, the rate of solvent evaporation is then controlled by the size of the flow control orifice 175 and the inlet to outlet pressure drop.

According to one embodiment, a gas is introduced into the space 170 through the inlet port 120. The gas can be a dry, inert gas such as, but not limited to, nitrogen. The gas introduced through the inlet port 120 can be at ambient pressure. Alternatively, the gas can be introduced at a pressure greater than ambient pressure, such as, for example, 5 pounds per square inch (psi) over ambient pressure. When the exhaust port 135 is closed, the gas flows from the inlet port 120 into the space 170 and solvent vapor accumulates in the head space 170 and the lower outlet tube 145.

Advantageously, the exhaust port 135 may be kept closed, then periodically opened to allow gas and solvent vapor to leave the space 170 and the device 100 through the exhaust port 135. When the exhaust port is opened, the gas introduced into the well 110 flushes a portion of the solvent vapor out of the space 170, through the exhaust port 135, and out of the device 100. The exhaust ports 135 associated with each row 160 may be independently and selectively opened at certain times and for certain periods of time based on the volatility of the solvents contained in each row.

During the time intervals when the exhaust port 135 is kept closed, the air in the space 170 can become saturated or nearly saturated with solvent vapor. In one embodiment, for example, the air in the space 170 reaches a high vapor concentration during the periods when the exhaust port 135 is closed. The air in the space 170 may approach 90 percent or even approximately 100 percent saturation. The degree of vapor saturation reached before the exhaust port 135 is opened can be selected and optimized to allow for a constant or near constant rate of evaporation of the solvent in the solution 165. For example, the maximum desired vapor saturation may be selected based on the particular volatility of the solution 165 in the well 110, and/or the similar volatility of solutions in the eight wells 110 in one row 160.

When the exhaust port 135 is opened, the gas can flow from the inlet port 120, to the space 170, then through the lower outlet tube 145, carrying a portion of the air with solvent vapor out of the space 170 as the gas flows to the exhaust port 135. When the exhaust port is open, the rate of flow of the solvent vapor out of the device 100 is determined mainly by the size of orifice 175, although the inlet to outlet pressure difference can have an effect on flow rate also.

The disk 150 can be made of any suitable material, including, but not limited to, sapphire. For example, sapphire disks with orifices are commercially available and suitable for use in embodiments of the device 100. In one embodiment, an orifice with a diameter of approximately 34 microns is drilled through a sapphire disk 150. As shown in FIG. 3, the precision-drilled portion of the disk 150 need not extend the entire length of the disk 150. It will be understood that the flow control orifice is a controlled, narrow-diameter region that can be located in any suitable portion of the disk 150. The diameter of the orifice can be selected to increase or decrease the rate at which gas and solvent vapor flow out of the space 170 to the exhaust port 135 when the port is opened. Thus, control over the flow of solvent vapor out of the device 100 is provided by selecting the pressure at the port(s) 120, 135, opening and closing the exhaust port 135 according to a selected duty cycle, and selecting the disk flow control orifice size.

It will be appreciated that the contribution of any one factor controlling flow of solvent vapor out of the device 100 can be more or less than the contribution of another factor controlling flow of vapor. Although it will be appreciated that these parameters may vary widely, in embodiments found to be especially advantageous, a disk flow control orifice size will be less than about 100 microns, and the input to output pressure difference may be about 10-20 pounds per square inch (psi). This results in a low flow rate when the exhaust port is open that is fairly insensitive to the presence of moderate changes or fluctuations in inlet to outlet pressure. This configuration is useful because the pressure differential is the least accurately controllable aspect of the system compared to disk orifice size and duty cycle timing. Because the orifice and duty cycle can be controlled with high accuracy, extremely accurate and repeatable control over solvent evaporation is possible.

Figure 4:
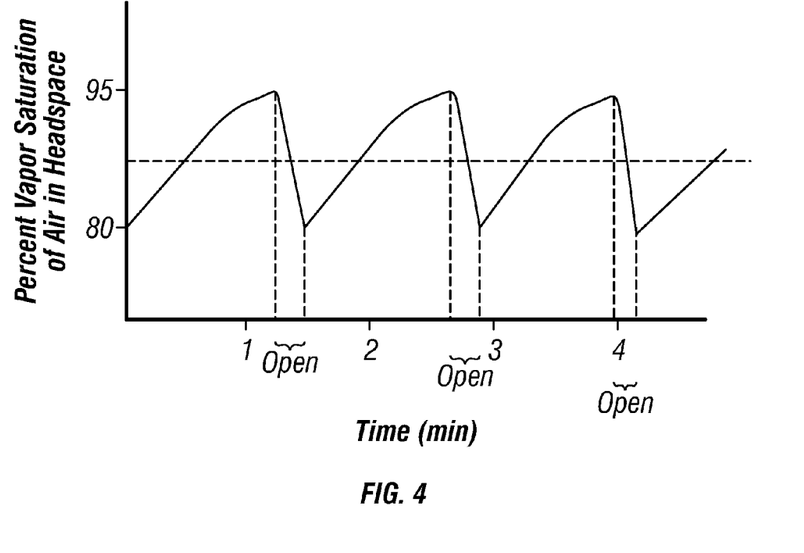
FIG. 4 is a graph of vapor saturation levels in one well in an embodiment of a controlled evaporation device.

Referring now to FIG. 4, the exhaust port 135 may be opened and closed at a selected duty cycle, to allow air with solvent vapor to leave the space 170 and the device 100. Thus, the evaporation of solvent from the solution 165 can be controlled wholly or in part by opening the exhaust port 135 according to this selected duty cycle. In one embodiment, for example, the duty cycle can be selected such that the air in the space 170 approaches 100 percent vapor saturation before the exhaust port 135 is opened. While the exhaust port is open, the orifice in the disk 150 limits the outflow of gas and solvent vapor from the space 170, such that only a portion of air saturated with vapor leaves the space 170. Then, the duty cycle can be timed to end such that the air in the space 170 is approximately 90 percent saturated with solvent vapor when the exhaust port 135 is closed.

The average saturation level of the air in the space 170 over the course of the evaporation process may be held nearly constant, and deviations from this average value are relatively small. The graph in FIG. 4 illustrates the nearly constant nature of the average saturation level according to one embodiment. In this example embodiment, the saturation level in the space 170 reaches approximately 95 percent before the start of each open time, then drops to approximately 80 percent at the end of each open time. After the exhaust port 135 is closed, the concentration of solvent in the space 170 begins increasing again and the saturation level begins rising above the lower limit of 80 percent. As the vapor saturation increases, the evaporation rate of the solvent slows but evaporation continues. The opening of the exhaust port 135 can be timed to begin before or just when evaporation of the solvent significantly slows or stops. Controlling the saturation level of the air in the space 170 such that it moves between two closely spaced saturation levels produces a constant or steady evaporation of solvent from the solution in the well 110.

The evaporation of the solvent with the methods and devices described herein is reproducible and efficient, as the solvent is not allowed to evaporate too quickly, preventing or hindering formation of high quality crystals, nor is the solvent allowed to evaporate too slowly, resulting in unnecessary delay in the evaporation process. In addition, embodiments of the present invention can be scaled to allow evaporation of a solvent from small volume wells such as, but not limited to, the wells in a 96-well plate, thus eliminating the drawbacks associated with holes in aluminum foil that can allow the solvent to evaporate too quickly and prevent formation of high quality drug crystals.

Furthermore, embodiments of the present invention can allow for the controlled evaporation of multiple solvents of varying volatilities in one plate 105 by separately controlling the evaporation rate for different sets of wells. As described above, in some embodiments each inlet port 120 is connected to and in fluid communication with only one row 160 and the wells 110 associated with that row, and each exhaust port 135 is connected to and in fluid communication with only one row 160 and the wells 110 associated with that row. In this embodiment, each row 160 is connected to one inlet port and one exhaust port. A given row may hold solutions comprising solvents of the same or similar volatility, but different from one or more other rows. The wells 110 associated with a given row, holding solutions of the same or similar volatility, receive the same gas at the same inlet-outlet pressure drop at the same exhaust duty cycle. A different row holding different solvents may receive the same or different gas at a different exhaust duty cycle. Different orifice sizes might also be provided for different wells or sets of wells, although this can be inconvenient in that different manifolds would be used for different plates. This is also generally unnecessary, as it has been found that duty cycle control is normally sufficient for good performance. It would also be possible to provide different pressure differentials, but as described above, this is generally a less advantageous method of evaporation control.

Thus, referring again to FIG. 1, the twelve wells 110 of a first row 160 may be filled with one solution comprising a very volatile solvent, and the twelve wells 110 of a second row 190 may be filled with a second solution comprising a relatively stable solvent. In another embodiment, the twelve wells 110 of the first row 160 are not filled with identical solutions, but with solutions of similarly high volatilities, and the twelve wells 110 of the second row 190 are filled with solutions comprising different but relatively stable solvents. The inlet port 120 and the exhaust port 135 associated with the first row 160, as well as the disks 150 associated with each well in the first row 160, control the evaporation of solvents from the solutions only in the first row 160. Similarly, the inlet port 120, the exhaust port 135, and the disks 150 associated with the second row 190, control the evaporation of solvents from the solutions only in the second row 190. Thus, evaporation of solvents from the solutions in the second row 190 can occur independently and unaffected by evaporation occurring in the first row 160. Thus, the pressure of the gas introduced into the wells, the duty cycle parameters, and the size of the orifice in the disks 150 can be independently selected and optimized for each row in the plate 105 based on the characteristics of the solvents in each row.

As noted above, embodiments of the present invention can also allow for the controlled evaporation of multiple solvents of the same, similar, or different volatilities from one well 110. For example, one well 110 can hold a solution comprising multiple, different solvents. Cosolvents are commonly used in the crystallization process to take advantage of the different volatilities and physical and/or chemical characteristics of the different solvents.

The device 100 may include an inlet pressure regulator that controls the pressure of the gas introduced into the inlet port 120 and a controller that controls the opening and closing of the exhaust valve 180, and thus the duty cycle, of a row 160. The controller can individually and separately control the opening and closing of the exhaust valves 180, and thus control the duty cycles, associated with multiple rows in the plate 105. In some aspects, the controller controls the opening and closing of the exhaust valves 180 according to programmed duty cycles. The programmed duty cycles can be selected and optimized as described above to ensure constant and/or steady evaporation of the solvent from the solution 165. Thus, according to some aspects, evaporation of a solvent from a solution can be automated or semi-automated, and result in consistent, reproducible results over multiple evaporation cycles.

Figure 5:
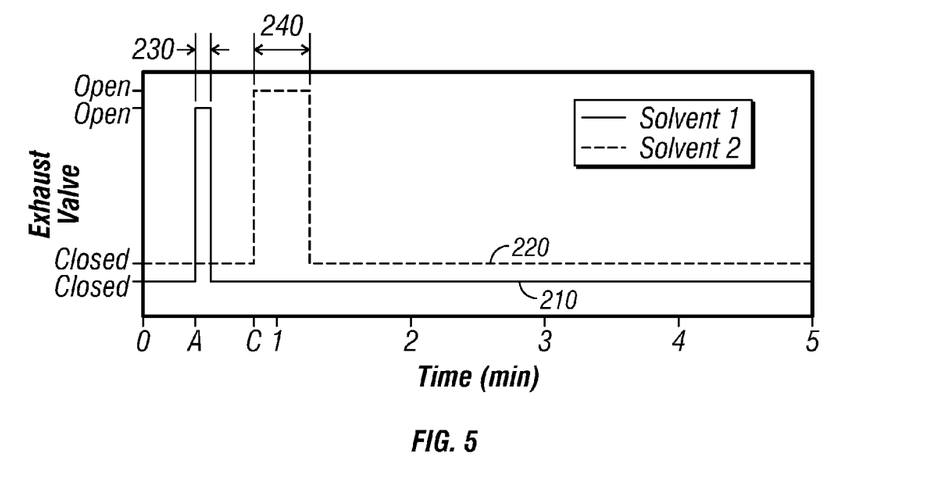
FIG. 5 is a graph of duty cycles for two solvents in an embodiment of a controlled evaporation device.

FIG. 5 illustrates selection of different duty cycles to optimize evaporation of two different solvents, Solvent 1 and Solvent 2. In the example embodiment illustrated in FIG. 5, Solvent 1 is more volatile than Solvent 2. Thus, after the exhaust ports 135 associated with Solvents 1 and 2 are closed following an open period, Solvent 1 begins to evaporate more quickly than Solvent 2. As a result, the air in the space 170 above Solvent 1 approaches saturation more quickly than the air over Solvent 2. To ensure the steady, slow evaporation of Solvent 1, the open period of cycle 210 for Solvent 1 is programmed to begin at a time A, before the open period of cycle 220 for Solvent 2 is programmed to begin. At a later time C, the air above Solvent 2 also approaches saturation. The open period of cycle 220 for Solvent 2 is thus programmed to begin at or around time C.

Because Solvent 1 is more volatile than Solvent 2, the vapor associated with Solvent 1 will have a higher concentration in the head space than the vapor associated with Solvent 2. Thus, opening the exhaust valves associated with Solvents 1 and 2 for the same amount of time would lead to more Solvent 1 vapor leaving the device compared to Solvent 2 vapor leaving the device. The evaporation rates of Solvents 1 and 2 can be matched or more closely aligned by programming the duration of the open period 230 for Solvent 1 to be less than the duration of the open period 240 for Solvent 2. When the exhaust valve associated with the less volatile Solvent 2 is opened, a less concentrated vapor leaves the device during a longer open period, such that approximately equal amounts of Solvent 1 vapor and Solvent 2 vapor leave the device, thereby equalizing evaporation rates.

Thus, according to some embodiments, the controller can cycle the exhaust valves 180 associated with each row 160 such that the evaporation of solvents with very different volatilities progresses at the same or a similar rate. As a result, solvents with dissimilar volatilities can be evaporated from the wells in a single plate 105 over the same or a very similar period of time, such that the various evaporation processes occurring in the plate 105 are timed to begin and end at roughly the same time. This can allow drug crystals to be collected from all of the wells 110 in the plate 105 at one time, freeing all of the wells 110 of the plate 105 at one time to be refilled with new solutions for evaporation.

Embodiments of the present invention also include controlling solvent evaporation by regulating the temperature of the plate 105. Changing the temperature of the plate 105 can change the evaporation rate of the solvent in the wells 110, and thus the solvent vapor pressure in the head space 170 between open periods. During evaporation, an external source can add heat to the endothermic evaporation process. The plate 105 can be heated by an external source, for example, such that the solutions 165 in the wells 110 are heated. In one embodiment, the temperature of plate 105 is increased for more volatile solutions with higher evaporation rates to maintain a constant solution temperature and solvent evaporation rate. In another embodiment, the evaporation rate of a solvent is increased or decreased by setting the plate temperature above or below room temperature.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. A device for controlled evaporation of solvent from at least one solution, comprising:
   a plurality of wells configured to hold the at least one solution;
   an inlet port for a first set of one or more of the plurality of wells;
   an exhaust port for a second set of one or more of the plurality of wells; and
   at least one flow control orifice positioned between the inlet port and the exhaust port.

2. The device of claim 1, wherein the flow control orifice is formed through a disk.

3. The device of claim 2, wherein the disk comprises sapphire.

4. The device of claim 1, wherein each of the plurality of wells in the first set comprises a head space located between the at least one solution and the inlet port, and wherein the orifice is configured to control the rate at which solvent vapor from a head space above the solution in at least one well flows to the exhaust port.

5. The device of claim 1, further comprising an inlet pressure regulator.

6. The device of claim 5, comprising at least one exhaust valve and a controller, wherein the controller is configured to control the at least one exhaust valve according to a programmed duty cycle.

7. The device of claim 1, wherein the wells are coated with an inert material.

8. The device of claim 1, wherein the plurality of wells is arranged in one or more rows and one or more columns.

9. The device of claim 8, wherein the first set of wells comprises a row or column of wells.

10. The device of claim 9, wherein the second set of wells comprises the same row or column of wells.

11. The device of claim 1, wherein the first and second sets comprise all of the plurality of wells.

12. The device of claim 1, wherein the first and second sets comprise some of the plurality of wells.

13. The device of claim 1, wherein the first set of wells holds a first solution and wherein the second set of wells holds a second solution, and wherein the first and second solutions are different.

14. The device of claim 8, wherein the plurality of wells is arranged in eight rows and twelve columns.

15. The device of claim 1, further comprising an external heat source.

16. A device for controlled evaporation of solvent from at least one solution, comprising:
   a plate comprising a plurality of wells, wherein a selected first set of wells hold a first solution comprising at least one solvent;
   a first gas inlet connected to and in fluid communication only with the selected first set of wells;
   a first vapor removal outlet connected to and in fluid communication only with the selected first set of wells;
   means for controlling the rate at which solvent vapor flows from the first set of wells to the vapor removal outlet.

17. The device of claim 16, wherein the flow rate controlling means comprises at least one orifice positioned between the gas inlet and the vapor removal outlet.

18. The device of claim 16, wherein the flow rate controlling means comprises a pressure regulator connected to the gas inlet.

19. The device of claim 16, wherein the flow rate controlling means comprises a valve connected to the vapor removal outlet.

20. The device of claim 19, wherein the flow rate controlling means further comprises a controller connected to the valve.

21. The device of claim 16, wherein the vapor removal outlet is subjected to a vacuum.

22. The device of claim 16, further comprising:
   a second gas inlet connected to and in fluid communication only with a selected second set of wells of the plate, wherein the second set of wells holds a second solution comprising at least one solvent;
   a second vapor removal outlet connected to and in fluid communication only with the selected second set of wells;
   means for controlling the rate at which solvent vapor flows from the second set of wells to the second vapor removal outlet, wherein the flow rate of solvent vapor from the second set of wells to the second vapor removal outlet is different than the flow rate of solvent vapor from the first set of wells to the first vapor removal outlet.

23. The device of claim 22, further comprising an external heat source.

24. A device for controlled evaporation of solvent from at least one solution, comprising:

a plate comprising a first set of wells and a second set of wells, wherein the first set of wells hold a solution comprising at least one first solvent and the second set of wells hold a different solution comprising at least one second solvent different from the at least one first solvent;

a set of gas inlets connected to and in fluid communication only with a corresponding set of wells;

a set of vapor removal outlets separately connected to and in fluid communication with the same corresponding set of wells;

means for separately controlling vapor removal from the first and second sets of wells.

25. The device of claim 24, wherein the means for separately controlling vapor removal comprises an orifice positioned between each gas inlet and each vapor removal outlet.

26. The device of claim 24, wherein the means for separately controlling vapor removal comprises a pressure regulator connected to each gas inlet.

27. The device of claim 24, wherein the means for separately controlling vapor removal comprises a valve connected to each vapor removal outlet.

28. The device of claim 24, wherein the means for separately controlling vapor removal comprises a controller connected to one or more valves.

29. The device of claim 24, wherein one or more vapor removal outlets is subjected to a vacuum.

30. The device of claim 24, further comprising an external heat source.

* * * * *